United States Patent
Habboushe

(10) Patent No.: US 9,226,891 B2
(45) Date of Patent: Jan. 5, 2016

(54) ANTI-FLUSH COMPOSITIONS

(71) Applicant: Vitalis LLC, Wilmington, DE (US)

(72) Inventor: Joseph Habboushe, New York, NY (US)

(73) Assignee: Vitalis LLC, Wilmington, DE (US)

( * ) Notice: Subject to any disclaimer, the term of this patent is extended or adjusted under 35 U.S.C. 154(b) by 359 days.

(21) Appl. No.: 13/659,196

(22) Filed: Oct. 24, 2012

(65) Prior Publication Data

US 2013/0115289 A1   May 9, 2013

Related U.S. Application Data

(60) Provisional application No. 61/552,852, filed on Oct. 28, 2011.

(51) Int. Cl.
| | | |
|---|---|---|
| A61K 6/00 | (2006.01) | |
| A61K 9/24 | (2006.01) | |
| A61K 31/44 | (2006.01) | |
| A61K 31/616 | (2006.01) | |
| A61K 31/455 | (2006.01) | |
| A61K 9/00 | (2006.01) | |

(52) U.S. Cl.
CPC ............ *A61K 9/0002* (2013.01); *A61K 9/0056* (2013.01); *A61K 9/209* (2013.01); *A61K 31/44* (2013.01); *A61K 31/455* (2013.01); *A61K 31/616* (2013.01)

(58) Field of Classification Search
None
See application file for complete search history.

(56) References Cited

U.S. PATENT DOCUMENTS

| | | |
|---|---|---|
| 4,814,181 A | 3/1989 | Jordan |
| 5,407,686 A | 4/1995 | Patel |
| 5,552,152 A | 9/1996 | Shen |
| 5,558,879 A | 9/1996 | Chen |
| 5,702,723 A | 12/1997 | Griffin |
| 5,981,555 A | 11/1999 | Kuhrts |
| 6,004,945 A | 12/1999 | Fukunaga |
| 6,060,078 A | 5/2000 | Lee |
| 6,114,370 A | 9/2000 | Wall, Jr. |
| 6,372,255 B1 | 4/2002 | Saslawski |

(Continued)

FOREIGN PATENT DOCUMENTS

| | | |
|---|---|---|
| EP | 1 260 216 | 11/2002 |
| EP | 1 498 140 | 1/2005 |

(Continued)

OTHER PUBLICATIONS

Campbell, JAMA 297: 2018-2024 (2007).*

(Continued)

*Primary Examiner* — Robert A Wax
*Assistant Examiner* — Thor Nielsen
(74) *Attorney, Agent, or Firm* — Sheppard Mullin Richter & Hampton LLP

(57) ABSTRACT

Disclosed are pharmaceutical compositions having a portion of aspirin for intraoral release and another aspirin for gastrointestinal release. The compositions can further include niacin. Methods of using such compositions to treat diseases or conditions suitably treated by niacin are also provided which result in reduced flushing.

31 Claims, 1 Drawing Sheet

(56) References Cited

U.S. PATENT DOCUMENTS

| | | | |
|---|---|---|---|
| 6,469,035 | B1 | 10/2002 | Cefali |
| 6,669,879 | B1 | 12/2003 | Spengler et al. |
| RE39,069 | E | 4/2006 | Faour |
| 8,263,125 | B2 | 9/2012 | Vaya et al. |
| 2002/0028826 | A1 | 3/2002 | Robl et al. |
| 2003/0035839 | A1 | 2/2003 | Hirsh |
| 2003/0104078 | A1 | 6/2003 | Barrett-Reis et al. |
| 2003/0180352 | A1 | 9/2003 | Patel et al. |
| 2004/0224020 | A1 | 11/2004 | Schoenhard |
| 2005/0045197 | A1 | 3/2005 | Gelder |
| 2005/0048164 | A1 | 3/2005 | Stahl |
| 2005/0148556 | A1 | 7/2005 | Tawakol |
| 2005/0249823 | A1 | 11/2005 | Murphy et al. |
| 2005/0267091 | A1 | 12/2005 | Berlin |
| 2006/0024365 | A1 | 2/2006 | Vaya et al. |
| 2006/0153916 | A1 | 7/2006 | Vaya et al. |
| 2006/0178398 | A1 | 8/2006 | Adams et al. |
| 2006/0275344 | A1 | 12/2006 | Mody et al. |
| 2006/0276416 | A1 | 12/2006 | Sinclair et al. |
| 2007/0072861 | A1 | 3/2007 | Roniker et al. |
| 2008/0050429 | A1 | 2/2008 | Rocca |
| 2008/0058292 | A1 | 3/2008 | Tawakol |
| 2009/0069275 | A1 | 3/2009 | Rocca et al. |
| 2009/0082315 | A1 | 3/2009 | Tawakol |
| 2009/0078483 | A1 | 9/2009 | Sison |
| 2009/0232886 | A1 | 9/2009 | Sison |
| 2010/0015220 | A1 | 1/2010 | Wetterau |
| 2010/0166810 | A1 | 7/2010 | Habboushe |
| 2011/0071185 | A1* | 3/2011 | Bunick et al. .............. 514/290 |
| 2013/0189361 | A1 | 7/2013 | Habboushe |

FOREIGN PATENT DOCUMENTS

| | | |
|---|---|---|
| EP | 1 743 644 | 1/2007 |
| WO | WO 99/11245 | 3/1999 |
| WO | WO 99/20110 | 4/1999 |
| WO | WO 2006/081624 | 6/2008 |
| WO | WO 2009/005803 | 1/2009 |
| WO | WO 2009/142731 | 11/2009 |

OTHER PUBLICATIONS

International Search Report and Written Opinion for PCT/US2012/061639, mailed Feb. 6, 2013.
International Search Report and Written Opinion for PCT/US2008/008191, mailed Sep. 26, 2008.
International Search Report and Written Opinion for PCT/US2010/061952, mailed Sep. 27, 2011.
Lai et al., "Suppression of Niacin-induced Vasodilation with an Antagonist to Prostaglandin D2 Receptor Subtype 1", Clinical Pharmacology & Therapeutics, 81:849-857, abstract, 2007.
U.S. Appl. No. 14/023,188, filed Sep. 10, 2013, Habboushe.
Benyo et al., "GPR109A (PUMA-G/HM74A) Mediates Nicotinic Acid-Induced Flushing," *The Journal of Clinical Investigation*, 2005, vol. 115, No. 12, pp. 3634-3640.
Catella-Lawson et al., "Cyclooxygenase Inhibitors and Antiplatelet Effects of Aspirin," *New England Journal of Medicine*, 2001, vol. 345, No. 25, pp. 1809-1817.
Fette, "PT 4090", Tablet Press, http://www.fette-compacting.de/cps/rde/xchg/fette_de_en/layout.xsl/343.html, 2010.
Hata, "HT-AP44-MSU-C", http://www.eliz.com/Hata/presses/php?layout=print, 2010.
Kilian, "RUD", Tablet Press, http://www.surplusolutions-lic.com/Equipment/ProcessingEquipment/TabletPresses/KilianRUDTabletPress.aspx, 2010.
Knopp et al., "Contrasting Effects of Unmodified and Time-Release Forms of Niacin on Lipoproteins in Hyperlipidemic Subjects: Clues to Mechanism of Action of Niacin," *Metabolism*, 1985, vol. 34, No. 7, p. 642-650.
Knopp, "Evaluating Nicain in its Various Forms," *The American Journal of Cardiology*, vol. 86, Issue 12 (1A), 2000, pp. 51-56.
Langman et al., "Risks of Bleeding Peptic Ulcer Associated with Individual Non-Steroidal Anti-Inflammatory Drugs," *The Lancet*, 1994, vol. 343, pp. 1075-1078.
Meyers et al., "Nicotinic Acid Induces Secretion of Prostaglandin $D_2$ in Human Macrophages: An in vitro Model of the Niacin Flush," *Atherosclerosis*, 2007, vol. 192, pp. 253-258, epub Sep. 1, 2006.

* cited by examiner

ANTI-FLUSH COMPOSITIONS

CROSS REFERENCE TO RELATED APPLICATIONS

This application claims the benefit under 35 U.S.C. §119(e) of U.S. Provisional Ser. No. 61/552,852, filed Oct. 28, 2011, the contents of which are incorporated by reference in their entirety into the current disclosure.

FIELD OF INVENTION

The present invention relates generally to the field of pharmaceutical compositions for oral administration, including a portion of aspirin for intraoral release such that this portion of aspirin can be delivered through transmucosal route, and another portion for gastrointestinal release.

BACKGROUND

Niacin (also known as vitamin B3, nicotinic acid and vitamin PP) is one of five vitamins associated with a pandemic deficiency disease: niacin deficiency (pellagra), vitamin C deficiency (scurvy), thiamin deficiency (beriberi), vitamin D deficiency (rickets), vitamin A deficiency (night blindness and other symptoms). Niacin has also been used to increase levels of HDL cholesterol in the blood, decrease levels of triglycerides in the blood, decrease levels of LDL in the blood, slow progression and, at times, cause regression of atherosclerotic plaque in arteries, and has been found to modestly decrease the risk of cardiovascular events and/or decrease cause of death in a number of controlled human trials.

Niacin administration, however, results in patients experiencing several side effects that have limited its widespread use. Most notably, the immediate release form of niacin (niacin IR) stimulates prostaglandin-mediated flushing of the face and trunk. The flush is usually felt within minutes (e.g., 15-20 minutes) after administration, but can stay for a period of days. In addition, the extended and sustained release (SR) forms cause the flushing reaction, although not to as great an extent. Patients experiencing the flushing side effect experience a diminution of symptoms over time and eventually develop a partial tolerance to the flushing, but not against the lipid-modifying effects. However, the level of discomfort is such that many patients stop therapy in the early period of treatment and never reach the tolerant stage. In addition, the typical dosing of niacin IR was three times per day, a factor that also contributed to low patient compliance.

Attempts have been made to mitigate the side effects of niacin IR, which is completely absorbed in 1-2 hours, with a sustained release form of niacin, i.e., niacin SR. The niacin SR, which requires a period of at least 12 hours for complete absorption, has met only modest success. It was observed that niacin SR was significantly less effective in modifying lipids than the IR form, and also was associated with an increased incidence of hepatotoxicity and gastrointestinal intolerance.

More recently, an intermediate or extended release form of niacin, niacin ER, has been developed that has an absorption rate in the 8-12 hour range. Niacin ER lowers the rate of flushing observed with niacin IR, and lowers the hepatotoxicity incidence seen with niacin SR. However niacin ER still has more hepatotoxicity and may have less efficacy than niacin IR.

It is known in the art that administering a non-steroidal anti-inflammation drug (NSAID), e.g., aspirin, from about 30 minutes to about 120 minutes prior to administering niacin IR can lower the flushing side effect. The dosing regimen of niacin IR, however, requires that it be taken three times per day, thereby requiring that a patient also take NSAID three times a day at specific time points. The need to take the medication six or more different time points is likely a major contributor to low compliance to niacin IR therapy.

Therefore, there is still a need to develop formulations that are effective in reducing or even eradicating the flushing side effect of niacin and at the same time helping patients to comply with the dosing requirements of the therapy.

SUMMARY

It has been discovered that oral administration of aspirin achieved a remarkably higher anti-flush effect when the aspirin is partially released intraorally and delivered transmucosally and partially released through the gastrointestinal (GI) track, as compared to intraoral or GI release alone. Further, such anti-flush effect is achieved even when niacin is concurrently administered, rather than given 30 minutes or more later. It is further contemplated that such finding can be extrapolated to other drugs that decrease niacin flush, in particular other NSAIDs or prodrugs or metabolites of NSAIDs that have similar exposure profiles between transmucosal delivery and GI release, as aspirin. Non limiting examples of such drugs include various cox inhibitors, NSAIDs (such as aspirin, ibuprofen, diclofenac, naproxen, keterolac, indocin, etc), salicylates (such as aspirin, salicin, salicylic acid, willow tree bark, etc), laropiprant, flavanoids (such as quercetin, luteolin, etc).

In accordance with one embodiment of the present disclosure, therefore, provided is a pharmaceutical composition comprising a first portion comprising a first subtherapeutic amount of aspirin, and a second portion comprising a second subtherapeutic amount of aspirin, wherein, upon oral administration to a subject, the first portion disintegrates or dissolves intraorally substantively providing rapid release of the aspirin of the first portion, and the second portion is substantially more difficult than the first portion to disintegrate or dissolve intraorally but is ingestible and releasable in the gastrointestinal track of the subject.

In another embodiment, the present disclosure provides a pharmaceutical composition comprising a first portion of aspirin and a second portion of aspirin, wherein the first portion comprises at least about 40% of a therapeutically effective amount of aspirin and is able to be intraorally absorbed and the second portion comprises at least about 40% of a therapeutically effective amount of aspirin, does not disintegrate or dissolve intraorally, and is gastrointestinally absorbed.

The pharmaceutical composition can be in the form of a tablet or capsule. In one aspect, the second portion is enclosed within the first portion. In one aspect, the first portion is chewable. In another aspect, the first portion is in the form of molded triturate.

In one aspect, the second portion is compressed. In another aspect, the hardness of the second portion is at least about 10 kilopascal (kp). In yet another aspect, the second portion further comprises a pharmaceutically acceptable flavoring agent not present in the first portion.

In any of the above embodiments, the pharmaceutical composition further comprises a third portion that comprises an effective amount of niacin. In one aspect, the third portion is in the form of controlled release. In another aspect, the third portion further comprises enteric coating. In still another aspect, the third portion is enclosed in the first portion or the second portion.

Another embodiment of the present disclosure provides a method of administering niacin to a subject with reduced flushing, comprising administering to the subject (a) an effective amount of niacin, (b) a first composition comprising a first subtherapeutic amount of aspirin and (c) a second composition comprising a second subtherapeutic amount of aspirin, wherein the first composition disintegrates or dissolves intraorally substantively providing rapid release of the aspirin of the first portion, and the second composition is ingested and released in the gastrointestinal track of the subject.

In one aspect, the niacin (a) is administered following the administration of (b) and (c). In another aspect, the niacin (a) is administered concurrently with (b) and (c). In one aspect, the niacin (a) is enclosed in a pharmaceutical composition that also comprises (b) and (c).

In one aspect of such a method, the administration is within 30 minutes following a meal. In another aspect, the administration is accompanied by oral administration of an acidic drink which can assist transmucosal absorption of the first aspirin composition.

Also provided is a method of administering aspirin to a subject with reduced side effects, comprising administering to the subject a first composition comprising a first subtherapeutic amount of aspirin and a second composition comprising a second subtherapeutic amount of aspirin, wherein the first composition disintegrates or dissolves intraorally within 10 minutes permitting rapid release of the aspirin in the first composition, and the second composition is ingested and released in the gastrointestinal track of the subject.

Still in another embodiment, provided is a method of administering aspirin to a subject with reduced side effects, comprising administering to the subject a therapeutically effective amount of aspirin, wherein a portion of the aspirin disintegrates or dissolves intraorally within 10 minutes, or alternatively within 5 minutes, 2 minutes, 1 minute, 50 seconds, 40 seconds, 30 seconds, 20 seconds or 10 seconds, permitting rapid release of the aspirin in the portion, and the remaining aspirin is ingested and released in the gastrointestinal track of the subject.

Either of these methods can further comprise administering to the subject an effective amount of niacin.

DETAILED DESCRIPTION

Figure 1:
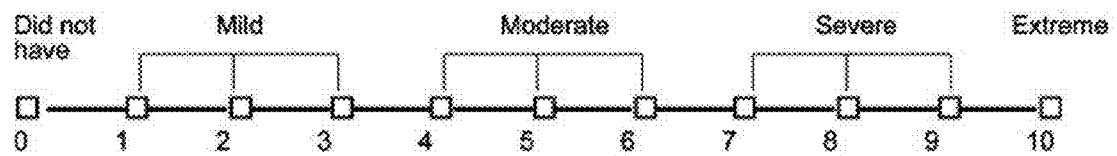
FIG. 1 illustrates the Global Flush Severity Scale used in Example 1.

The present disclosure provides pharmaceutical compositions for oral administration of aspirin and niacin for reducing the flushing side effects of niacin. One aspect of the disclosure relates to the discovery that oral administration of aspirin achieved a remarkably higher anti-flush effect when the aspirin is partially released intraorally and partially released through the gastrointestinal (GI) track, as compared to intraoral or GI release alone. Thus, in one embodiment, the present disclosure provides a unit dosage form containing a portion of aspirin for intraoral release and another portion of aspirin for GI release.

A. Definitions

Unless defined otherwise, the terms used herein are intended to have their ordinary meaning in the art.

All numerical designations, e.g., pH, temperature, time, concentration, and weight, including ranges, are approximations that typically may be varied (+) or (−) by increments of 0.1, 1.0, 10.0, or 100.0 as appropriate. It is to be understood, although not always explicitly stated, that all numerical designations are preceded by the term "about".

"About" will be understood by persons of ordinary skill in the art and will vary to some extent on the context in which the term is used. If there are uses of the term which are not clear to persons of ordinary skill in the art given the context in which it is used, "about" will mean up to plus or minus 10%, or 5%, or 2% or 1% or 0.5% of the particular term.

As used herein, the term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

As used in the specification and claims, the singular form "a", "an", and "the" includes plural references unless the context clearly dictates otherwise.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

As used herein, "compressed" dosage form (e.g., "compressed portion"), refers to a dosage form comprising a compressed powder. For example, a compressed portion may be formed using a rotary tablet press or other similar machinery known to one of skill in the art.

As used here, "disintegrates or dissolves intraorally" refers to that a majority of a composition or a portion of a composition, such as a tablet or a capsule, breaks apart into smaller particles intraorally. The majority, in one aspect, means at least about 50%, or alternatively at about 60%, or 70%, or 80%, or 90%, or 95%, or 98%, or 99%.

As used herein, "bilayer" compressed dosage form (e.g., "bilayer tablet") refers to a single compressed dosage form comprising two layers. A bilayer compressed dosage form can be made in a single compression step. Likewise, a "trilayer" compressed dosage form (e.g., "trilayer tablet") refers to a single compressed dosage form comprising three layers.

As used herein, "wet granulation" refers to a process known in the pharmaceutical arts that involves forming granules by the addition of a liquid, such as purified water, alcohol, or a binder solution.

"Controlled release form" refers to a formulation in which the niacin is included within a matrix, which matrix can be either insoluble, soluble, or partly soluble. Controlled release matrix formulations of the insoluble type are also referred to as insoluble polymer matrices, swellable matrices, or lipid matrices depending on the components that make up the matrix. Controlled release matrix formulations of the soluble type are also referred to as hydrophilic colloid matrices, erodible matrices, or reservoir systems. Controlled release formulations of the present disclosure refer to formulations comprising an insoluble matrix, a soluble matrix or a combination of insoluble and soluble matrices in which the rate of release is slower than that of an uncoated non-matrix or immediate release formulations or uncoated normal release matrix formulations. Controlled release formulations can be coated with a control releasing coat to further slow the release of niacin from the controlled release matrix formulation. Such coated controlled release matrix formulations can exhibit modified-release, controlled-release, sustained-release, extended-release, prolonged-release, delayed-release, or combinations thereof, of niacin. Examples of controlled release forms of niacin include Slo-Niacin® available from Upsher Smith Laboratories, Inc. (Maple Grove, Minn.).

"Controlled release coat" refers to a functional coat which can, for example, include at least one pH independent or pH dependent (such as for example enteric or reverse enteric types) polymer, soluble or insoluble polymer, lipids or lipidic materials, or combinations thereof, which, when applied onto a formulation can slow (for example, when applied to an immediate release formulation or a normal release matrix formulation), further slow (for example when applied to a controlled release matrix formulation), or modify the rate of release of niacin.

"Excipient" refers to a pharmacologically inactive substance used with the active agents or drugs of a medication or a formulation. Excipients are also sometimes used to bulk up formulations that contain very potent active ingredients, to allow for convenient and accurate dosage. In addition to their use in the unit dose forms, excipients can be used in the manufacturing process to aid in the handling of the active substance concerned. Depending on the route of administration, and form of medication, different excipients may be used. Examples of an excipient includes, without limitation, one or more of the following: an additive, an anti-foaming agent, a binder, a chemical stabilizer, a coloring agent, a diluent, a disintegrating agent, an emulsifying agent, a filler, a flavoring agents, a glidant, a lubricant, a pH modifier, a plasticizer, a solubilizer, a swelling enhancer, a spheronization aid, a solubility enhancer, or a suspending agent.

"Immediate release formulation" refers to a formulation from which the drug is released without any substantial delay and substantially at once.

"Patient" or "subject" refers to mammals, including humans and animals, such as simians, cattle, horses, dogs, cats, and rodents having the need to take niacin.

"Pharmaceutically acceptable salt" refers to pharmaceutically acceptable salts derived from a variety of organic and inorganic counter ions well known in the art that include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use, 2002, incorporated herein by reference.

"Plasticizer" refers to a compound capable of plasticizing or softening a polymer or a binder. Plasticizers can broaden the average molecular weight of a polymer in which they are included thereby lowering its glass transition temperature or softening point. Plasticizers also can reduce the viscosity of a polymer. The use of plasticizers is optional, but they can be included in a formulation to modify the properties and characteristics of the polymers used in the coat(s) or core of the formulation for convenient processing during manufacture of the coat(s) and/or the core of the formulation. Once the coat (s) and/or core has been manufactured, certain plasticizers can function to increase the hydrophilicity of the coat(s) and/or the core of the formulation in the environment of use. During manufacture of the coat(s) and/or core, the plasticizer can lower the melting temperature or glass transition temperature (softening point temperature) of the polymer or binder.

"Solid formulation" refers to a formulation that is neither liquid nor gaseous. Solid formulations include tablets, powders, microparticles, capsules, matrix forms, suppositories, sachets, troches, patches and lozenges. Solid formulations in the form of capsules contain a solid composition within a capsule that can be made of gelatin or other encapsulating material. Liquid formulations include liquid suspensions and elixirs.

"Swelling enhancer" refers to an excipient that swells rapidly resulting in an increase in the size of the tablet. At lower concentrations, these excipients can be used as super disintegrants; however at higher concentrations, e.g., at concentrations above about 5% w/w, these excipients function as swelling enhancers and increase the size of the matrix formulation.

"Therapeutically effective amount" refers to an amount of the drug that, when administered to a patient, will have the intended therapeutic effect, e.g., alleviation, amelioration, palliation or elimination of one or more manifestations of cancer or other hyperproliferative disease in the patient. A therapeutic effect does not necessarily occur by administration of one dose, and may occur only after administration of a series of doses. Typically, cancer drugs are administered in a repeating series of doses, and in certain instances each series may be referred to as a "cycle" of therapy. Thus, a therapeutically effective amount may be administered in one or more administrations.

The term "subtherapeutic amount" or "synergistically therapeutic amount" typically refers to a less than standard therapeutic amount of a drug, meaning that the amount required for the desired effect is lower than when the drug is used alone. In one aspect, the subtherapeutic amount varies depending on the desired effect. In this respect, therefore, the subtherapeutic amount of a drug for one desired effect may be actually higher than the therapeutic amount of the same drug for another desired effect. In one aspect, a subtherapeutic amount is at least about 20%, or 30%, or 40%, or 50%, or 60%, or 70, or 80%, or 90% of a therapeutically effective amount.

"Treating" or "treatment of" a condition or patient refers to taking steps to obtain beneficial or desired results, including clinical results. For purposes of this invention, beneficial or desired clinical results include, but are not limited to, in intended treatment purpose of niacin such as increasing HDL or lowering LDL or other beneficial results including reduction of side effects such as flushing. Other beneficial results of niacin include meliorating niacin deficiency, decreasing levels of Triglycerides in the blood, slowing progression and causing regression of atherosclerotic plaque in arteries, decreasing the risk of cardiovascular events, and decreasing overall cause of death.

B. Oral Dosage Forms

As shown in Example 1, patients in Period IV (500 mg niacin +81 mg aspirin, half-swallowed and half-mucosally-absorbed) experienced the least severe flushing side effects, with a Global Flush Severity Scale (GFSS) average score: 3.94. This is in comparison with Period III (500 mg niacin+81 aspirin mucosally-absorbed/GFSS: 5.06) and Period II (500 mg niacin+81 aspirin swallowed/GFSS: 6.88). Further, during all periods in which aspirin was co-administered with niacin, the patients experienced less severe flush as compared to during Period I (500 mg niacin alone/GFSS: 8.44).

Such data indicate that the partial intraoral release and partial GI release of aspirin achieved a synergistic effect in reducing the flushing side effects of niacin. It is contemplated that GI-absorbed aspirin has a different metabolic profile from intraorally absorbed aspirin which directly enters into the blood stream. This is likely due to the first-pass metabolism of the liver for medication absorbed through the GI track.

Specifically, aspirin given directly into the blood stream results in a fast peak of serum aspirin concentration, which immediately begins to drop. The immediate drop is due to the fast metabolism of aspirin into its primary metabolite, salicylic acid, resulting in high serum levels of salicylic acid. Such a quick drop, therefore, is not favorable for aspirin's anti-flush effect.

Further, salicylic acid is a reversible COX inhibitor, and is known to act competitively with aspirin itself, which is an irreversible COX inhibitor. Therefore it is further contemplated that a directly-absorbed aspirin, like those IV or intraorally absorbed, not only leads to a time limited anti-flush effect, but actually hinders the anti-flush effect of aspirin.

GI-absorbed aspirin follows a different metabolic profile, with aspirin serum levels not peaking until approximately 15-20 minutes following administration. GI-absorbed aspirin is metabolized much more slowly than aspirin given directly into the blood stream. This allows for a longer time for aspirin's irreversible COX inhibitory effect to act upon the COX receptors, in the platelets as well as the vasculature.

Directly-absorbed (such as oral mucosally absorbed) aspirin has not yet been used to create an anti-flush effect for niacin. The present disclosure, however, reveals that not only was directly-absorbed aspirin effective in reducing the flushing side effect of niacin, there was a more pronounced anti-flush effect of aspirin given concurrently with niacin when this aspirin is partially absorbed through the oral mucosa (i.e. more directly into the blood stream without first-pass liver metabolism) and partially absorbed through the GI (i.e. undergoing first-pass liver metabolism).

Accordingly, these data suggest that aspirin absorbed directly into the blood stream hits a peak serum concentration relatively quickly, within minutes. Aspirin given concurrently through the GI, on the other hand, has a serum peak concentration about 15-20 minutes later. As the former metabolizes much quicker than the latter, there then is a point after ingestion—around 30-45 minutes, when the serum aspirin given by the former means is less then that given by the latter.

Therefore, when just focusing on the aspirin serum levels, a combination of direct-absorption and GI-absorption will "smooth out" the aspirin serum concentration over time: the direct absorption getting serum levels high early, and the GI absorption keeping serums level high later. This higher and wider serum level of aspirin result in a more pronounced anti-flush effect.

It is further contemplated that further delay between release of the aspirin and the release of niacin can help further reduce flush. Therefore, in some embodiments, it is contemplated that the administration of niacin is made after the patient has recently (e.g., within about 30 minutes) had a meal. In another embodiment, the delay can be achieved by enteric-coating the niacin portion of the pill. In such a case, the fast-absorption of aspirin through the oral mucosa leads to an earlier blockage of the COX receptors, early enough to give the most ideal 30-120 minute delay leading to an ideal anti-flush effect.

The data also suggest that elimination of salicylic acid from the serum is rather quick, with most of the elimination occurring within 20 minutes. Therefore, the peak concentration from GI-absorbed aspirin is delayed, relative to the oral mucosal-absorbed aspirin. Accordingly, there is less competitive inhibition by the former's salicylic acid metabolite than what would have been expected. This is more likely in the circumstance when the drugs were given to a patient after the patient recently had a meal.

It is also contemplated that a portion of GI absorbed aspirin turns into salicylic acid before the portion that remains as aspirin has time to block the vasculature COX, therefore partially competitively inhibiting itself more than it would for the platelet COX. An earlier, directly-absorbed aspirin bolus, in this respect, also has an added anti-flush effect through vasculature COX inhibition.

The data presented in the present disclosure also show that, by partially releasing aspirin intraorally and partially releasing aspirin through the GI, the combined effect is higher than what is achieved by separate administration due to the smoothened and broadened plasma exposure profile. Accordingly, such combined dosing also give rise to reduced side effects that would normally have occurred with either intraoral or GI formulation alone. Thus, one embodiment of the present disclosure provides methods of reducing aspirin-induced side effects, such as GI ulcer.

As noted above, one embodiment of the present disclosure provides a pharmaceutical composition comprising a first portion comprising a first subtherapeutic amount of aspirin, and a second portion comprising a second subtherapeutic amount of aspirin, wherein, upon oral administration to a subject, the first portion disintegrates or dissolves intraorally providing rapid release of the aspirin of the first portion, and the second portion is substantially more difficult than the first portion to disintegrate or dissolve intraorally but is ingestible and releasable in the gastrointestinal track of the subject.

In one aspect, the aspirin of the first portion is at a subtherapeutic amount, such as but not limited to, from about 10 mg to about 1000 mg. In one aspect, the amount of aspirin of the first portion is at least about 10 mg, or least about 20 mg, 30 mg, 40 mg, 50 mg, or 100 mg. In another aspect, the amount of aspirin of the first portion is no more than about 150 mg, 200 mg, 250 mg, 300 mg, 325 mg, 400 mg, 500 mg, 600 mg or 650 mg. In one aspect, the aspirin in the second portion is at a subtherapeutic amount, such as but not limited to, from about 10 mg to about 1000 mg. In one aspect, the amount of aspirin in the second portion is at least about 10 mg, or least about 20 mg, 30 mg, 40 mg, 50 mg, or 100 mg. In another aspect, the amount of aspirin in the second portion is no more than about 150 mg, 200 mg, 250 mg, 300 mg, 325 mg, 400 mg, 500 mg, 600 mg or 650 mg.

In one aspect, the aspirin of the first portion is at least about 10%, or 20%, or 30%, or 40%, of 50%, or 60%, or 70%, or 80%, or 80% of a therapeutically effective amount. In one aspect, the aspirin of the first portion is at most about 10%, or 20%, or 30%, or 40%, of 50%, or 60%, or 70%, or 80%, or 80% of a therapeutically effective amount. In one aspect, the aspirin of the second portion is at least about 10%, or 20%, or 30%, or 40%, of 50%, or 60%, or 70%, or 80%, or 80% of a therapeutically effective amount. In one aspect, the aspirin of the second portion is at most about 10%, or 20%, or 30%, or 40%, of 50%, or 60%, or 70%, or 80%, or 80% of a therapeutically effective amount.

In one aspect, the first portion of aspirin constitutes at least about 10% of the total aspirin. Alternatively, the first portion of aspirin constitutes at least about 20%, or 30%, or 40%, or 50%, or 60%, or 70%, or 80%, or 90% of the total aspirin. In some aspects, however, the first portion of aspirin can be less than about 20%, or 30%, or 40%, or 50%, or 60%, or 70%, or 80%, or 90% of the total aspirin. In a particular aspect, the first portion constitutes from about 40% to about 60%, or alternatively from about 45% to about 55% of the total aspirin.

In one aspect, the total amount of aspirin in the composition is less than about 50 mg, or 60 mg, or 70 mg, or 80 mg, or 90 mg, or 100 mg, or 120 mg, or 140 mg, or 150 mg, or 160 mg, or 165 mg, or 170 mg, or 180 mg, or 190 mg, or 200 mg. In another aspect, the total amount of aspirin in the composition is greater than about 150 mg, 160 mg, or 165 mg, or 170 mg, or 180 mg, or 190 mg, or 200 mg, or 250 mg, or 300 mg, or 400 mg, or 500 mg, or 600 mg, or 700 mg, or 800 mg, or 900 mg, or 1000 mg.

In yet another aspect, the therapeutically effective amount of niacin is about 100 mg, or about 200 mg, or about 300 mg, or about 400 mg, or about 500 mg, or about 600 mg, or about 700 mg, or about 800 mg, or about 900 mg, or about 1000 mg, or about 2000 mg, or about 3000 mg. In one aspect, the therapeutically effective amount of niacin is higher than what is normally given to a patients, such as higher than about 400 mg, about 500 mg, about 600 mg, about 700 mg, about 800 mg, about 900 mg, about 1000 mg, about 2000 mg, or about 3000 mg.

In one aspect, the total aspirin in the composition is at least about 81 mg. In one aspect, the first portion contains at least about 40 mg aspirin and the second portion contains at least about 40 mg aspirin. In some aspects, the second portion also contains at least about 500 mg niacin. In another aspect, the total aspirin in the composition is at least about 162 mg. In one aspect, the first portion contains at least about 81 mg aspirin and the second portion contains at least about 81 mg aspirin. In some aspects, the second portion also contains at least about 1000 mg niacin.

In one aspect, the total aspirin in the composition is at least about 121 mg. In one aspect, the first portion contains at least about 60 mg aspirin and the second portion contains at least about 60 mg aspirin. In some aspects, the second portion also contains at least about 500 mg niacin. In another aspect, the total aspirin in the composition is at least about 242 mg. In one aspect, the first portion contains at least about 121 mg aspirin and the second portion contains at least about 121 mg aspirin. In some aspects, the second portion also contains at least about 1000 mg niacin.

In one aspect, the total aspirin in the composition is at least about 203 mg. In one aspect, the first portion contains at least about 101 mg aspirin and the second portion contains at least about 101 mg aspirin. In some aspects, the second portion also contains at least about 500 mg niacin. In another aspect, the total aspirin in the composition is at least about 406 mg. In one aspect, the first portion contains at least about 203 mg aspirin and the second portion contains at least about 203 mg aspirin. In some aspects, the second portion also contains at least about 1000 mg niacin.

In one aspect, the ratio between the total aspirin and niacin in the composition is about 81/1000, 81/500 or 162/500. In another aspect, the ratio between the total aspirin and niacin in the composition is at least about 1/20, 81/1000, 1/10, 81/500, 1/5, 162/500, 1/4, 1/3, 1/2, or 1. In another aspect, the ratio between the total aspirin and niacin in the composition is not higher than about 1/20, 81/1000, 1/10, 81/500, 1/5, 162/500, 1/4, 1/3, 1/2, or 1.

The compositions of the present disclosure are clearly distinguishable from what has been disclosed in the prior art, in which only one type of aspirin formulation is used, see, e.g., US 2010/0166810. On the other hand, the disclosure of US 2010/0166810 is incorporated as reference into the present disclosure to more fully describe compositions and methods suitable for preparing the compositions of the present disclosure.

Another aspect of the invention provides a process of preparing the disclosed compositions. In some embodiments, the process comprises forming a first portion and a second portion and compressing the first and second portions to form a bilayer or two-halves compressed solid oral dosage form. Preparation of each portion is further described below.

1. First Portion of Aspirin for Intraoral Release

Methods of preparing a composition suitable for intraoral release are known in the art. In one aspect, the first portion further includes a film-coating agent, an excipient, a binder, a lubricant, or a plasticizer.

In one aspect, the first portion disintegrates or dissolves intraorally within about 10 minutes. In other aspects, the first portion disintegrates or dissolves intraorally within about 9 minutes, or about 8, or about 7, or about 6, or about 5, or about 4, or about 3 or about 2 minutes, or alternatively about 60 seconds, or about 50, or about 40, or about 30, or about 20, or about 10, or about 5 seconds.

In some aspects, the first portion is chewable. In some aspects, the first portion is in the form of molded triturate.

In one aspect, the first portion further includes an agent that promotes the oral or buccal absorption of aspirin. Non-limiting examples of such agents include bile acid salts, sodium lauryl sulfate, lysalbinic acid, salicylic acid, 5-methoxy salicylic acid, 3,4-dihydroxy phenyl acetic acid (DOPAC) and homovanillic acid and their sodium salts thereof. Other hydroxyaryl acids, such as 1-hydroxy-2-naphthoic acid, naphthoresorcyclic acid, ferulic acid, caffeic acid, resorcylic acid and gentisic acid, have similar effects.

The amount of hydroxyaryl or hydroxyaralkyl acid or salt, amide or ester derivatives thereof forms may vary over a wide range; in general, the identity and the amount of the hydroxyaryl or hydroxyaralkyl acids or salt, amide or ester thereof is used in connection with the drug in order to be effective in enhancing the absorption rate of the drug into the bloodstream.

In another aspect, the first portion further includes a disintegrant. Non-limiting examples of diintegrants include crospovidone, crystalline cellulose, hydroxypropylcellulose with a low degree of substitution, croscarmellose sodium, carmellose calcium, carboxystarch sodium, carboxymethyl starch sodium, potato starch, wheat starch, corn starch, rice starch, partly pregelatinized starch, and hydroxypropyl starch. One or two or more of these can be used together. Coating with a disintegrant also contributes to improvement of compression moldability.

2. Second Portion of Aspirin, and Optionally Third Portion of Niacin, for GI Release The second and third portions of the composition can be prepared with methods known in the art for a typical oral dosage form suitable for GI absorption. Like the first portion, the second portion can also include a film-coating agent, an excipient, a binder, a lubricant, or a plasticizer.

Compared to the first portion, the second is substantially more difficult to disintegrate or dissolve intraorally. This can be achieved chemically or physically. For instance, the second portion can be physically harder. In one aspect, the second portion is compressed. In another aspect, the second portion has a hardness that is at least about 10 kilopascal (kp), or alternatively about 11, or 12, or 13, or 14, or 15, or 20, or 25 or 30 or 40 or 50 kp.

Hardness can be assessed by means commonly used in the art, for example, using commercially available hardness testers that are routinely used for assessing the hardness of pharmaceutical dosage forms.

In some aspects, the second portion further comprises a pharmaceutically acceptable flavoring agent not present in the first portion. The flavoring agent provides a flavor that alerts the patients that this portion should not be chewed and needs to be swallowed so as to increase patient compliance.

In one aspect, the aspirin in the second portion constitutes at least about 10% of the total aspirin. Alternatively, the aspirin in the second portion constitutes at least about 20%, or 30%, or 40%, or 50%, or 60%, or 70%, or 80%, or 90% of the total aspirin. In some aspects, however, the aspirin in the second portion can be less than about 20%, or 30%, or 40%, or 50%, or 60%, or 70%, or 80%, or 90% of the total aspirin. In a particular aspect, the aspirin in second portion constitutes from about 40% to about 60%, or alternatively from about 45% to about 55% of the total aspirin. In one aspect, the ratio of aspirin between the first portion and the second portion is about 1:1. Alternatively, the ratio is at least about 1:4, or 1:3, or 1:2 or 1:1.5, or is no more than about 4:1, 3:1, 2:1 or 1.5:1.

The pharmaceutical composition of the present disclosure can be in the form of a tablet or capsule. When in the form of a tablet, the second portion, in one aspect, is enclosed within the first portion or alternatively partially exposed.

When the composition is in the form of a tablet, the tablet can include an outer portion and an inter portion, with the outer portion containing the first portion and the inner portion containing the second portion and optionally the third portion.

In one aspect, the outer portion is formulated to dissolve in the oral cavity of a subject and to release the aspirin in the first portion across the oral mucosa of the subject. In one aspect, the inner portion is harder than the outer portion and is formulated for dissolving in stomach, intestines, or further distal in the gastrointestinal tract of the subject.

In one aspect, the inner portion comprises a texture on the surface that is recognizable by the tongue of a subject. In another aspect, the outer portion comprises a water soluble sugar or sugar substitute. In another aspect, the outer portion is surrounded by a thin shell to allow encapsulation of liquid, powder or gel in the outer portion.

In one aspect, the outer potion is flavored or sweetened. In one aspect, the tablet further comprises an intermediate layer between the outer and inner portions. In one aspect, the intermediate layer comprises enteric coating. In one aspect, the inner portion is formulated to absorb a biting shock and not break a tooth. In another aspect, the tablet comprises a layer of aspirin which breaks down in the mouth, but this layer has particles within it that don't completely break down in the mouth and stay full particles, such that there is partial intraoral release and, when the particles as swallowed, partial gastrointestinal release.

The pharmaceutical composition of the above embodiments can further include a third portion that comprises an effective amount of niacin. In one aspect, the third portion is in the form of controlled release. In another aspect, the third portion further comprises enteric coating. In yet another aspect, the third portion is enclosed in the first portion or the second portion.

3. Additional Additives to the Composition

In yet another aspect, either or both of the first portion and second portion further comprises excipients, lubricants, pH adjusters, taste-masking agents, sweeteners, acidifiers, refrigerants, foaming agents, preservatives, fluidizers, antioxidants, colorants, stabilizers, surfactants, buffering agents, flavors, binders or drug solubilizers. A person skilled in the art may immediately list specific examples of these additives.

Any excipient used for pharmaceutical preparations can be used without limitation, but examples of excipients used in the tablet of the present invention can include sugars such as erythritol, mannitol, xylitol, sorbitol, lactitol, paratinit, paratinose, maltitol, maltose, trehalose, lactose, sucrose, glucose, olygosaccharides, fructose and maltose and the like. One or two or more kinds of these excipients can be used.

Various embodiments of the composition may include pharmaceutically acceptable binders (adhesives). Binders are agents that impart cohesive properties to powdered materials through particle-particle bonding. Examples of suitable binders include celluloses and crosslinked polyvinyl pyrrolidone, matrix binders (dry starch, dry sugars), film binders (polyvinyl pyrrolidone (PVP), starch paste, celluloses, bentonite, sucrose), and chemical binders (polymeric cellulose derivatives, such as carboxy methyl cellulose, hydroxypropylcellulose (HPC) and hydroxypropylmethylcellulose (HPMC); sugar syrups; corn syrup; water soluble polysaccharides such as acacia, tragacanth, guar and alginates; gelatin; gelatin hydrolysate; agar; sucrose; dextrose; and non-cellulosic binders, such as polyvinyl pyrrolidone, polyethylene glycol (PEG), vinyl pyrrolidone copolymers, pregelatinized starch, sorbitol, glucose, microcrystalline cellulose, such as FMC BioPolymer's Avicel® PH101 and Avicel® PH102, and silicified microcrystalline cellulose, such as Penwest Pharmaceutical's ProSolv SMCC™). In specific embodiments, a binder is selected from the group consisting of corn starch, potato starch, polyvinyl pyrrolidone, hydroxypropylmethyl cellulose, and hydroxylpropyl cellulose. A binder may be included in any portion of the dosage form, such as the intragranular portion and/or extragranular portion of either or both of the first and second layers.

In some embodiments, the composition further comprises a pharmaceutically acceptable diluent or filler. Pharmaceutically acceptable diluents include, but are not limited to, lactose (such as lactose monohydrate, lactose anhydrous, and DMV International's Pharmatose® DCL21 crystalline alpha monohydrate milled lactose), mannitol, talc, magnesium stearate, sodium chloride, potassium chloride, citric acid, spray-dried lactose, starch, hydrolyzed starches, directly compressible starch, microcrystalline cellulose (such as Avicel® PH101 and Avicel® PH102), cellulosics, sorbitol, sucrose, glucose, sucrose-based materials, saccharides, calcium sulfate, dibasic calcium phosphate (such as Emcompress®) and dextrose, and/or mixtures of any of the foregoing. In specific embodiments, a diluent is selected from the group consisting of microcrystalline cellulose, lactose, mannitol, dicalcium phosphate, dextrose, compressible sugar, and spray-dried lactose with microcrystalline cellulose. A diluent may be may be included in any portion of the dosage form, such as the intragranular portion and/or extragranular portion of either or both of the first and second layers.

In some embodiments, the composition comprises magnesium stearate. In specific embodiments, the magnesium stearate is present in a range of about 0.5% to 2% w/w, based on the total weight of the layer.

In some embodiments, the diluent is microcrystalline cellulose or microlac (spray-dried lactose with microcrystalline cellulose). In specific embodiments, the microcrystalline cellulose or microlac is present in a range of about 20% to 60% w/w, based on the total weight of the layer.

Various embodiments of the invention may include pharmaceutically acceptable anti-adherents (anti-sticking agents, glidants, flow promoters, lubricants) such as talc, colloidal silicon dioxide, such as Aerosil® 200, magnesium stearate, fumed silica (Carbosil, Aerosil), micronized silica (Syloid No. FP 244, Grace U.S.A.), polyethylene glycols, surfactants, waxes, stearic acid, stearic acid salts, stearic acid derivatives, calcium stearate, silica gel, starch, hydrogenated vegetable oils, sodium benzoate, sodium acetate, leucine, PEG-4000, and magnesium lauryl sulfate. In specific embodiments, an anti-adherents is selected from glidants and lubricants. Suitable glidants include, but are not limited to, colloidal silicon dioxide (Aerosil®), magnesium trisilicate, talc, and tribasic calcium phosphate. Suitable lubricants include, but are not limited to magnesium, aluminum, calcium, zinc stearate, and talc. An anti-adherent may be included in any portion of the dosage form, such as the intragranular portion and/or extragranular portion of either or both of the first and second layers. In specific embodiments, an anti-adherent is included in the extragranular portion of the first layer and/or the extragranular portion of the second layer.

In some embodiments, the glidant is talc. In specific embodiments, talc is present in a range of about 1% to 7% w/w, based on the total weight of each layer.

C. Therapeutic Methods

Therapeutic methods are also provided. In one aspect, provided is a method of administering niacin to a subject with reduced flushing, comprising administering to the subject (a) an effective amount of niacin, (b) a first composition comprising a first subtherapeutic amount of aspirin and (c) a second portion comprising a second subtherapeutic amount of aspirin, wherein the first composition disintegrates or dissolves intraorally providing rapid release of the aspirin of the first portion, and the second composition is ingested and released in the gastrointestinal track of the subject.

In one aspect, the first portion disintegrates or dissolves intraorally within about 10 minutes. In other aspects, the first portion disintegrates or dissolves intraorally within about 9 minutes, or about 8, or about 7, or about 6, or about 5, or about 4, or about 3 or about 2 minutes, or alternatively about 60 seconds, or about 50, or about 40, or about 30, or about 20, or about 10, or about 5 seconds. In another aspect, the first portion is absorbed transmucosally in the oral cavity within about 10 minutes, or about 9, or about 8, or about 7, or about 6, or about 5, or about 4, or about 3 or about 2 minutes, or alternatively about 60 seconds, or about 50, or about 40, or about 30, or about 20, or about 10, or about 5 seconds.

In one aspect, the aspirin in (b) is a subtherapeutic amount, such as but not limited to, from about 10 mg to about 1000 mg. In one aspect, the aspirin in (b) is at least about 10 mg, or at least about 20 mg, 30 mg, 40 mg, 50 mg, or 100 mg. In another aspect, the aspirin in (b) is no more than about 150 mg, 200 mg, 250 mg, 300 mg, 325 mg, 400 mg, 500 mg, 600 mg or 650 mg. In one aspect, the aspirin in (c) is a subtherapeutic amount, such as but not limited to, from about 10 mg to about 1000 mg. In one aspect, the aspirin in (c) is at least about 10 mg, or least about 20 mg, 30 mg, 40 mg, 50 mg, or 100 mg. In another aspect, the aspirin in (c) is no more than about 150 mg, 200 mg, 250 mg, 300 mg, 325 mg, 400 mg, 500 mg, 600 mg or 650 mg. In another aspect, the aspirin in both (b) and (c) is a subtherapeutic amount, such as but not limited to, from about 10 mg to about 1000 mg, or is at least about 10 mg, or least about 20 mg, 30 mg, 40 mg, 50 mg, or 100 mg, or is no more than about 150 mg, 200 mg, 250 mg, 300 mg, 325 mg, 400 mg, 500 mg, 600 mg or 650 mg.

In one aspect, the aspirin in (b) is at least about 10%, or 20%, or 30%, or 40%, of 50%, or 60%, or 70%, or 80%, or 80% of a therapeutically effective amount. In one aspect, the aspirin in (b) is at most about 10%, or 20%, or 30%, or 40%, of 50%, or 60%, or 70%, or 80%, or 80% of a therapeutically effective amount. In one aspect, the aspirin in (c) is at least about 10%, or 20%, or 30%, or 40%, of 50%, or 60%, or 70%, or 80%, or 80% of a therapeutically effective amount. In one aspect, the aspirin of in (c) is at most about 10%, or 20%, or 30%, or 40%, of 50%, or 60%, or 70%, or 80%, or 80% of a therapeutically effective amount.

In one aspect, the aspirin in (b) constitutes at least about 10% of the total aspirin. Alternatively, the aspirin in (b) constitutes at least about 20%, or 30%, or 40%, or 50%, or 60%, or 70%, or 80%, or 90% of the total aspirin. In some aspects, however, the aspirin in (b) can be less than about 20%, or 30%, or 40%, or 50%, or 60%, or 70%, or 80%, or 90% of the total aspirin. In a particular aspect, the aspirin in (b) constitutes from about 40% to about 60%, or alternatively from about 45% to about 55% of the total aspirin.

In one aspect, the total amount of aspirin in the composition is less than about 50 mg, or 60 mg, or 70 mg, or 80 mg, or 90 mg, or 100 mg, or 120 mg, or 140 mg, or 150 mg, or 160 mg, or 165 mg, or 170 mg, or 180 mg, or 190 mg, or 200 mg. In another aspect, the total amount of aspirin in the composition is greater than about 150 mg, 160 mg, or 165 mg, or 170 mg, or 180 mg, or 190 mg, or 200 mg, or 250 mg, or 300 mg, or 400 mg, or 500 mg, or 600 mg, or 700 mg, or 800 mg, or 900 mg, or 1000 mg.

In yet another aspect, the therapeutically effective amount of niacin is about 100 mg, or about 200 mg, or about 300 mg, or about 400 mg, or about 500 mg, or about 600 mg, or about 700 mg, or about 800 mg, or about 900 mg, or about 1000 mg, or about 2000 mg, or about 3000 mg. In one aspect, the therapeutically effective amount of niacin is higher than what is normally given to a patient, such as higher than about 400 mg, about 500 mg, about 600 mg, about 700 mg, about 800 mg, about 900 mg, about 1000 mg, about 2000 mg, or about 3000 mg.

In one aspect, the niacin (a) is administered following the administration of (b) and (c). In another aspect, the niacin (a) is administered concurrently with (b) and (c). In another aspect, (b) and (c) are in a single dosage form as disclosed above in the disclosure. In another aspect, the niacin (a) is also in the same dosage form as (b) and (c). In some embodiments, the administration is with 30 minutes following a meal. In another aspect, the administration is accompanied by oral administration of an acidic drink which can assist transmucosal absorption of the first aspirin composition.

In one aspect, the niacin is absorbed in the GI track at least about 10 minutes after the transmucosal absorption of the first portion of the aspirin. In another aspect, the niacin is absorbed at least about 11, 12, 13, 14, 15, 20, 25, 30, 40, 50 or 60 minutes after transmucosal absorption of the first portion of the aspirin.

Also, methods are provided that comprises administering any composition of the present disclosure to a subject. Such methods are useful for reducing the flushing side effects of niacin or any side effects caused by aspirin, such as GI ulcer.

Also provided, therefore, is a method of administering aspirin to a subject with reduced side effects, comprising administering to the subject a first composition comprising a first subtherapeutic amount of aspirin and a second composition comprising a second subtherapeutic amount of aspirin, wherein the first composition disintegrates or dissolves intraorally within 10 minutes permitting rapid release of the aspirin of the first portion, and the second composition is ingested and released in the gastrointestinal track of the subject.

It is also contemplated that a single composition of aspirin can also be used to achieve the desired effect, when a portion of the aspirin is dissolved intraorally and the remaining is released in the GI track. Such a composition of aspirin can be combined with niacin. In one aspect, the aspirin forms an outer layer with the niacin being in the inner layer.

Thus, also provided is a method of administering aspirin to a subject with reduced side effects, comprising administering to the subject a therapeutically effective amount of aspirin, wherein a portion of the aspirin disintegrates or dissolves intraorally within 10 minutes permitting rapid release of the aspirin in the portion, and the remaining aspirin is ingested and released in the gastrointestinal track of the subject.

In other aspects, the first composition or portion of the aspirin disintegrates or dissolves intraorally within about 9 minutes, or about 8, or about 7, or about 6, or about 5, or about 4, or about 3 or about 2 minutes, or alternatively about 60 seconds, or about 50, or about 40, or about 30, or about 20, or about 10, or about 5 seconds.

In any embodiment of the above methods, the method further comprises administering to the subject an effective amount of niacin.

Yet another embodiment provides a method of treating a disease or condition in a subject that is suitably treated by niacin with reduced flushing side effects. Such diseases and conditions are known in the art. For instance, it is known that niacin is effective in treating or ameliorating dyslipidemia (e.g., HDL, LDL, triglycerides). Further, niacin helps the body fight off bacterial infections, including Methicillin-resistant Staphylococcus aureus (MRSA) infections.

Moreover, niacin increases a patient's neutrophil count. This is especially important for those with neutropenia (low neutrophils) which is often caused by chemotherapy—one of the more deadly side effects of chemo. Therefore the present compositions can be used as an adjuvant in chemotherapy for prophylaxis to neutropenia. The present compositions and methods are particular useful because the normal side effects of chemotherapy may make typical high-dose niacin untolerable to most patients.

Newer evidence also suggests that niacin has an anti-atherosclerosis mechanism (decreases arterial plaques which cause heart attacks and death) that is distinct and separate from niacin's effect on dyslipidemia. This is consistent with some older studies where the HDL, LDL, Triglycerides will not change as much as with other meds but there are larger decreases in plaques. Further, recent animal evidence shows niacin can cause a decrease in inflammation in the lungs, which could have therapeutic uses in many lung diseases (e.g., COPD, Asthma, ILD, ARDS, CF, etc). Treatment of these disease and conditions, therefore, are all within the scope of the present disclosure.

Example 1

This example demonstrates the anti-flush effect of concurrent administration of both intraorally released and gastrointestinal tract (GI) released aspirin.

Healthy human patients were recruited for this study. Each patient did not have an allergy or reaction to aspirin or niacin, had not been diagnosed with kidney disease or liver disease, were not pregnant or planning to be pregnant within the following two months, had not been breastfeeding within the preceding two months, and had not used aspirin for the preceding 7 days.

In Period I, each patient was given 500 mg niacin orally. Each patient was asked to rate his or her flush on the Global Flush Severity Scale (GFSS) (see FIG. 1 and Paolini et al. *Int. J. Clin. Pract.* 62(6):896-904 (2008)), when the flush completely resolved. The Global Flushing Severity Score measures, overall, in the previous 24 hours, how each patient rates the flushing symptoms, including redness, warmth, tingling, and itchiness of the skin.

Period II did not start until at least two days upon completion of Period I. At Period II, each patient orally swallowed 81 mg aspirin followed by 500 mg niacin. After the flush completely resolved, then each patient recorded his or her GFSS flush rating.

Not until at least two days later did Period III start. At Period III, each patient was asked to not swallow the orally administered aspirin (81 mg) but to allow the aspirin to be absorbed through the oral mucosa. The aspirin was in powdered form and the remaining aspirin in the mouth was washed out with water. Afterwards, 500 mg of niacin was swallowed with a glass of water. Still, the flush was rated (GFSS) after it was resolved.

Still, at least another two days later, at Period IV, the patients were instructed to take mucosally-absorbable aspirin (81 mg) into the mouth, and chew partially and rub into the gums, lips and inside of mouth until about half dissolved (about 10 seconds), then swallow the rest with a glass of water. Then, each patient swallowed a dose of niacin (500 mg) with a glass of water. The flush was then rated (GFSS) after it completely resolved.

Figure 2:
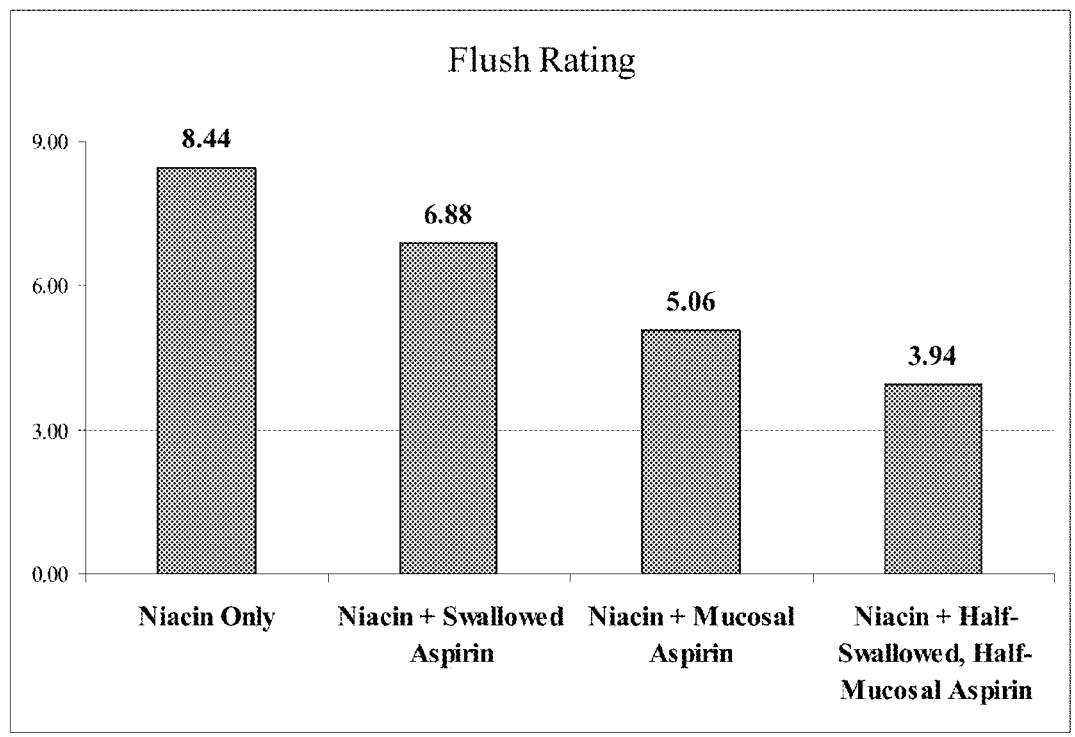
FIG. 2 presents the flush rates experienced by patients as described in Example 1 and shows that patients receiving both intraorally released and gastrointestinally released aspirin had the highest anti-flush effect.

As shown in FIG. 2, the patients during Period IV suffered the least severe flush (3.94, a 53% reduction from Period I) than during any other Period. Among Periods I through III, the severity of flush was the lowest in Period III (5.06, a 40% reduction from Period I), second lowest in Period II (6.88, a 18% reduction from Period I) and the highest in Period I (8.44). As the total amount of aspirin was the same among Period II-IV, this example therefore demonstrates the synergistic effect between intraorally released aspirin and GI-released aspirin.

Example 2

This example assesses the level of flushes caused by several combinations of niacin and agents having anti-flush effects, including aspirin and willow bark.

Study Design

After administration of a screening questionnaire, this study will enroll healthy volunteers meeting inclusion criteria into a cross-over study designed to measure the GFSS at specific time intervals after ingestion of the following regimens.

Standardizing Dose: [Niacin 1000 mg].

Group A: [Chewed Aspirin 162 mg]+[Swallowed Placebo 162 mg]+[Niacin 1000 mg]

Group B: [Chewed Placebo 162 mg]+[Swallowed Aspirin 162 mg]+[Niacin 1000 mg]

Group C: [Chewed Aspirin 81 mg+Chewed Placebo 81 mg]+[Swallowed Aspirin 81 mg+Swallowed Placebo 81 mg]+[Niacin 1000 mg]

Group D: [Chewed Willow Bark 400 mg]+[Swallowed Placebo 162 mg]+[Niacin 1000 mg].

Subjects will each first be given a single, immediate-release dose of 1000 mg of niacin alone, (a "calibration dose") and asked to rate the resultant flush, in order to give them the sense for how strongly the niacin flush is as a basis for comparison.

Then, after at least 24 hours (a "washout period") have passed, subjects will be given the above dosing regimens in a double-blind fashion, and asked to rate their flush at 30-minute intervals using a modified version of the GFSS (a 0-10 rating score) until the flush is completely reduced, or for three hours. Soda will be used for the chewable pills to improve mucosal absorption. Dosing of the medications will be at least 2 days apart, to allow for aspirin and willow bark elimination. The study will take approximately 3 hours per dosing, with 5 total doses spaced at least two days apart, to allow for a wash out period. The total study duration will be one-two weeks.

Inclusion criteria: Adults, age 18 or older.

Exclusion criteria: known allergy to aspirin, niacin or willow bark; known renal disease; known liver disease; known pregnancy; breast-feeding; and use of aspirin in the last 7 days.

Materials: All subjects will receive the same over-the-counter medications, such as Niacin (B3) 1000 mg capsules (Twinlab), White willow bark 400 mg tablets (Nature's Way, standardized), and aspirin (Bayer chewable low dose 81 mg;). A placebo similar to 81 mg aspirin will also be given, Statistical Analysis: Powering to detect an approximate 10% reduction in flush will require approximately 22 subjects. Assuming a 40% drop out rate, we will target the recruitment of 40 subjects.

Using the modified GFSS, each subject reports a flushing score from 1 to 10 (none 0, mild 1 to 3, moderate 4 to 6, severe 7 to 9, extreme 10), at 30 minute intervals, for the duration of the flushing sensation, up to 3 hours. The study will calculate a sum total flush score for each patient on each dosing regimen, as well as record each significant flushing event (a score of 4 or higher). The length of flush duration will also be recorded. These data will be compared between each regimen in each individual subject, and also compared amongst all subjects.

Primary Endpoint: Reduction in total flush score when compared with niacin alone.

Secondary Endpoints: Reduction in number of significant flushing events, and as a representation of the duration of the flush.

It is contemplated that Group C that includes both chewed and swallowed aspirin leads to the most flush reduction for niacin.

Example 3

This example is similar to Example 2, but uses different amounts of aspirin and niacin. In this example, each dosing regimen has a total of 203 mg aspirin. One dose has 203 mg of chewable aspirin, and a swallowed placebo, and 500 mg niacin. Another dosing has 203 mg of swallowed aspirin, and chewable placebo, and 500 mg niacin. A third dosing has 122 mg of chewable aspirin, 81 mg of swallowed aspirin, and 500 mg niacin. The niacin in each dosing period is 500 mg. In addition to being used with the chewable pills, soda can also be used for the washout.

Additionally, different from Example 2, the niacin pills used in this example have an enteric coating to further delay the release. It is noted that the enteric coating delays the release, rather than extends the release duration. It is contemplated that the dosing regiment that includes both chewed and swallowed aspirin will cause the most flush reduction for niacin.

It will be apparent to those skilled in the art that various modifications and variations can be made in the methods and compositions of the present invention without departing from the spirit or scope of the invention. Thus, it is intended that the present invention cover the modifications and variations of this invention provided they come within the scope of the appended claims and their equivalents.

The invention claimed is:

1. A pharmaceutical composition comprising a first portion comprising a first amount of aspirin, and a second portion comprising a second amount of aspirin, wherein the first portion and the second portion are formulated such that, upon oral administration to a subject, the first portion disintegrates or dissolves intraorally providing rapid release of the aspirin of the first portion, and the second portion is substantially more difficult than the first portion to disintegrate or dissolve intraorally but is ingestible and releasable in the gastrointestinal track of the subject, and wherein the first amount of aspirin and the second amount of aspirin each constitutes at least 20% of the total amount of aspirin in the composition.

2. The pharmaceutical composition of claim 1, in the form of a tablet or capsule.

3. The pharmaceutical composition of claim 1, wherein the second portion is enclosed within the first portion.

4. The pharmaceutical composition of claim 1, wherein the first portion is chewable.

5. The pharmaceutical composition of claim 1, wherein the first portion is in the form of molded triturate.

6. The pharmaceutical composition of claim 1, wherein the second portion is compressed.

7. The pharmaceutical composition of claim 1, wherein the hardness of the second portion is at least about 10 kilopascal (kp).

8. The pharmaceutical composition of claim 1, wherein the second portion further comprises a pharmaceutically acceptable flavoring agent not present in the first portion.

9. The pharmaceutical composition of claim 1, further comprising a third portion that comprises an effective amount of niacin.

10. The pharmaceutical composition of claim 9, wherein the third portion is in the form of controlled release.

11. The pharmaceutical composition of claim 10, wherein the third portion further comprises enteric coating.

12. The pharmaceutical composition of claim 9, wherein the third portion is enclosed in the first portion or the second portion.

13. A method of administering niacin to a subject with reduced flushing, comprising administering to the subject (a) an effective amount of niacin, (b) a first composition comprising a first amount of aspirin and (c) a second composition comprising a second amount of aspirin, wherein the first composition disintegrates or dissolves intraorally providing rapid release of the aspirin of the first portion, and the second composition is ingested and released in the gastrointestinal track of the subject, and wherein the first amount of aspirin and the second amount of aspirin each constitutes at least 20% of the total amount of aspirin administered.

14. The method of claim 13, wherein the niacin (a) is administered following the administration of (b) and (c).

15. The method of claim 14, wherein the niacin (a) is administered concurrently with (b) and (c).

16. The method of claim 15, wherein the niacin (a) is enclosed in a pharmaceutical composition that also comprises (b) and (c).

17. The method of claim 13, wherein the administration is with 30 minutes following a meal.

18. A method of administering aspirin to a subject with reduced side effects, comprising administering to the subject a first composition comprising a first amount of aspirin and a second composition comprising a second amount of aspirin, wherein the first composition disintegrates or dissolves intraorally within 10 minutes permitting rapid release of the aspirin of the first portion, and the second composition is ingested and released in the gastrointestinal track of the subject, and wherein the first amount of aspirin and the second amount of aspirin each constitutes at least 20% of the total amount of aspirin administered.

19. A method of administering aspirin to a subject with reduced side effects, comprising administering to the subject a therapeutically effective amount of aspirin, wherein a portion of the aspirin disintegrates or dissolves intraorally within 10 minutes permitting rapid release of the aspirin in the portion, and the remaining aspirin is ingested and released in the gastrointestinal track of the subject, and wherein the portion of aspirin and the remaining portion of aspirin each constitutes at least 20% of the total amount of aspirin administered.

20. The method of claim 19, further comprising administering to the subject an effective amount of niacin.

21. A tablet comprising:

(a) an outer portion comprising at least about 40 mg aspirin; and (b) an inner portion comprising at least about 40 mg aspirin, wherein the outer portion is formulated to dissolve in the oral cavity of a subject and to release the aspirin across the oral mucosa of the subject, and wherein the inner portion is harder than the outer portion and is formulated for dissolving in stomach, intestines, or further distal in the gastrointestinal tract of the subject.

22. The tablet of claim 21, wherein the inner portion comprises a texture on the surface that is recognizable by the tongue of a subject.

23. The tablet of claim 21, wherein the outer potion is flavored or sweetened.

24. The tablet of claim 21, wherein the outer portion further comprises a water soluble sugar or sugar substitute.

25. The tablet of claim 21, wherein the outer portion is surrounded by a thin shell.

26. The tablet of claim 25, wherein the outer portion further comprises liquid, gel or powder.

27. The tablet of claim 21, further comprising an intermediate layer between the outer and inner portions.

28. The tablet of claim 27, wherein the intermediate layer comprises enteric coating.

29. The tablet of claim 21, wherein the inner portion can absorb a biting shock and not break a tooth.

30. The tablet of claim 21, wherein the inner portion further comprises niacin.

31. The tablet of claim 30, wherein the inner portion comprises at least about 500 mg niacin.

* * * * *